(12) United States Patent
Au-Yeung et al.

(10) Patent No.: US 7,771,945 B2
(45) Date of Patent: Aug. 10, 2010

(54) APPARATUS AND METHOD FOR PREPARATIVE SCALE PURIFICATION OF NUCLEIC ACIDS

(76) Inventors: Kwok-Leung (Jacky) Au-Yeung, 2564 San Jose Ave., San Francisco, CA (US) 94112; Lee B Bussey, 1561 Ascension Dr., San Mateo, CA (US) 94402

( * ) Notice: Subject to any disclaimer, the term of this patent is extended or adjusted under 35 U.S.C. 154(b) by 0 days.

(21) Appl. No.: 11/965,607

(22) Filed: Dec. 27, 2007

(65) Prior Publication Data

US 2008/0102519 A1 May 1, 2008

Related U.S. Application Data

(62) Division of application No. 10/527,618, filed as application No. PCT/US03/28759 on Sep. 12, 2003, now Pat. No. 7,314,746.

(60) Provisional application No. 60/410,617, filed on Sep. 13, 2002.

(51) Int. Cl.
*C12Q 1/68* (2006.01)
*C12N 7/02* (2006.01)

(52) U.S. Cl. .......................... 435/6; 435/239
(58) Field of Classification Search ....................... None
See application file for complete search history.

(56) References Cited

U.S. PATENT DOCUMENTS

| | | | |
|---|---|---|---|
| 3,286,992 A | 11/1966 | Armeniades et al. | |
| 3,928,642 A | 12/1975 | Hubert et al. | 426/521 |
| 4,450,103 A | 5/1984 | Konrad et al. | 260/112 |
| 4,462,940 A | 7/1984 | Hanisch et al. | 260/112 |
| 4,490,259 A * | 12/1984 | Coffing | 210/704 |
| 4,621,061 A | 11/1986 | Pühler et al. | 435/320 |
| 4,623,723 A | 11/1986 | Keller et al. | 536/27 |
| 4,780,210 A | 10/1988 | Hsia | 210/638 |
| 4,830,969 A | 5/1989 | Holmes | 435/259 |
| 4,900,677 A | 2/1990 | Hewitt | 435/259 |
| 4,985,552 A | 1/1991 | Fedeli et al. | 536/27 |
| 4,997,932 A | 3/1991 | Reardon et al. | 536/27 |
| 5,008,189 A | 4/1991 | Oroskar et al. | 435/105 |
| 5,034,314 A | 7/1991 | Geiger et al. | 435/6 |
| 5,057,426 A | 10/1991 | Henco et al. | 435/270 |
| 5,096,818 A | 3/1992 | DeBonnville | 435/91 |
| 5,208,160 A | 5/1993 | Kikyotani et al. | 435/270 |
| 5,256,294 A | 10/1993 | Van Reis | 210/637 |
| 5,300,433 A | 4/1994 | Hrinda et al. | 435/238 |
| 5,561,064 A | 10/1996 | Marquet et al. | 435/320.1 |
| 5,576,196 A | 11/1996 | Horn et al. | 435/91.1 |
| 5,707,812 A | 1/1998 | Horn | 435/6 |
| 5,792,651 A | 8/1998 | Colpan et al. | 435/270 |
| 5,837,529 A | 11/1998 | Wan et al. | 435/259 |
| 5,916,775 A | 6/1999 | Hayashizaki | 435/91.1 |
| 5,981,735 A | 11/1999 | Thatcher et al. | 536/25.4 |
| 5,990,301 A | 11/1999 | Colpan et al. | 536/25.4 |
| 6,011,148 A | 1/2000 | Bussey et al. | 536/25.4 |
| 6,036,940 A | 3/2000 | Ju et al. | 424/9.52 |
| 6,152,358 A * | 11/2000 | Bryan | 229/87.19 |
| 6,197,553 B1 * | 3/2001 | Lee et al. | 435/91.1 |
| 6,214,586 B1 | 4/2001 | McNeilly | 435/91.1 |
| 6,268,492 B1 | 7/2001 | Mittelstaedt et al. | 536/25.4 |
| 6,277,648 B1 | 8/2001 | Colpan | 436/177 |
| 6,297,371 B1 | 10/2001 | Colpan et al. | 536/25.3 |
| 6,313,285 B1 | 11/2001 | Butler et al. | 536/25.4 |
| 6,492,164 B1 | 12/2002 | Crouzet et al. | 435/320.1 |
| 6,503,738 B1 | 1/2003 | Thatcher et al. | 435/91.1 |
| 6,617,443 B2 | 9/2003 | Hendriks et al. | 536/25.41 |
| 6,664,049 B1 | 12/2003 | Chevalier | 435/6 |
| 6,730,781 B1 | 5/2004 | Wils et al. | 536/25.4 |
| 6,750,333 B1 | 6/2004 | Kuhne | 536/23.1 |
| 6,825,012 B2 | 11/2004 | Blanche et al. | 435/91.42 |
| 7,026,468 B2 | 4/2006 | Nochumson et al. | 536/25.4 |
| 2001/0045359 A1 | 11/2001 | Cheng et al. | 204/547 |
| 2002/0198372 A1 * | 12/2002 | Bridenbaugh et al. | 536/25.4 |

FOREIGN PATENT DOCUMENTS

| | | |
|---|---|---|
| CA | 2474436 | 8/2003 |
| EP | 0 240 191 | 10/1987 |
| EP | 0 376 080 | 7/1990 |
| EP | 0 431 905 | 6/1991 |
| EP | 0 517 515 | 12/1992 |
| WO | WO 98/11208 | 3/1998 |
| WO | WO 98/30685 | 7/1998 |

(Continued)

OTHER PUBLICATIONS

Bioscience Contract Production Corp Flyer, "Plasmid DNA Production," (Jun. 1999).

(Continued)

*Primary Examiner*—Young J Kim
(74) *Attorney, Agent, or Firm*—D. Benjamin Borson

(57) ABSTRACT

Apparatus and methods are described for pharmaceutical grade manufacture extrachromosomal nucleic acids from cell lysates using flotation to separate and eliminate undesired insoluble cellular debris including chromosomal DNA from the lysates. A gas is introduced to controllably generate bubbles that reduce the density of the cell debris and create a buoyant flocculent phase that can be readily separated from, and thus provide, a substantially clarified fluid lysate phase that is enriched in extrachromosomal DNA but substantially depleted of cellular proteins and chromosomal DNA.

10 Claims, 7 Drawing Sheets

FOREIGN PATENT DOCUMENTS

| | | |
|---|---|---|
| WO | WO 99/55837 | 11/1999 |
| WO | WO 99/63076 | 12/1999 |

OTHER PUBLICATIONS

Birnboim, et al., "A Rapid Alkaline Extraction Procedure for Screening Recombinant Plasmid DNA," Nucleic Acids Res. 7, pp. 1513-1523 (1979).

Carlson, et al., "Mechanical Description of *Escherichia coli* for Plasmid Recovery," Biotechnology and Bioengineering 48, pp. 303-315 (1995).

Ciccolini et al., "Rheological Properties of Chromosomal and Plasmid DNA During Alkaline Lysis Reaction," Trends in Biotechnology 18, pp. 231-237 (1999).

Chandra, et al., "Large-Scale Purification of Plasmid DNA by Fast Protein Liquid Chromatography Using a High-Load Q Sepharose Column," Analytical Biochemistry 203, pp. 169-172 (1992).

Coppella, et al., "Isolation of High-Molecular-Weight Nucleic Acids for Copy Number Analysis Using High-Performance Liquid Chromatography," Journal of Chromatography 402, pp. 189-199, (1987).

Data Sheet TMAE (M), "Properties of the Tentacle Ion-Exchange Sorbents," http://www.chromatography.co.uk.products/bio/ds01.htm Aug. 26, 2003.

Davis, et al., Short Technical Reports, "Comparison of Plasmid DNA Preparation Methods for Direct Gene Transfer and Genetic Immunization," Biotechniques 21, pp. 93-99, (Jul. 1996).

Durland, et al., "Manufacturing and Quality Control of Plasmid-Based Expression Systems," Advanced Drug Delivery Reviews 30, pp. 33-48, (1998) Elsevier.

Ferreira, et al., "Downstream Processing of Plasmid DNA for Gene Therapy and DNA Vaccine Applications," Trends in Biotechnology 18, pp. 380-388 (Sep. 2000).

Fractogel EMD Process Media Merck KGaA 8 pages, (Sep. 1999).

"Guide to Tentacle-Biochromatography Products," http://www.chromatography.co.uk/products/bio/summary.htm, (Aug. 26, 2003).

Horn, et al., "Cancer Gene Therapy Using Plasmid DNA: Purification of DNA for human Clinical Trials," Human Gene Therapy 6, pp. 565-573 (May 1995).

Kahn, et al., "Purification of Plasmid DNA by Tangential Flow Filtration," Biotechnology and Bioengineering 69(1), pp. 101-106 (2000).

Kenics, "Kenics Static Mixer Systems," 4 pages (Mar. 1, 1995).

Lengsfeld, et al., "Shear-Induced Degradation of Plasmid DNA," J Pharmaceutical Sciences 91, pp. 1581-1589 (Jul. 2002).

Lesney, "It's Not Being Green?" Today's Chemist at Work, pp. 33-34 (Jul. 2002).

Levy et al., "Biochemical Engineering Approaches to the Challenges of Producing Pure Plasmid DNA" Trends of Biotechnology 18, pp. 296-305, (2000).

Maniatis, et al., "Large-Scale Isolation of Plasmid DNA, Molecular Cloning: A Laboratory Manual," pp. 85, 87, 90 and 91, (1982).

Marquet, et al., "Process Development for the Manufacture of Plasmid DNA Vectors for Use in Gene Therapy," BioPharm 8(7), pp. 26-37, (1995).

Marquet, et al., "Characterization of Plasmid DNA Vectors for use in Human Gene Therapy Part 1," BioPharm, pp. 42-50 (May 1997).

Merion, et al., "Purification of Supercoiled Plasmids from Crude Cell Lysates Using High Performance Anion Exchange Chromatography," BioTechniques 7(1), pp. 60-67, (1989).

Montbriand, et al., "Improved Method for the Removal of Endotoxin from DNA," Journal of Biotechnology 44, pp. 43-46, (1996).

pAlliance Brochure—QIAGENews, "Contract Plasmid DNA Manufacturing Services for Clinical and Commercial Applications" Issue No. 2, (2000).

Prazeres, et al., "Large-Scale Production of Pharmaceutical-Grade Plasmid DNA for Gene Therapy: Problems and bottlenecks," Trends Biotechnol. 17, pp. 169-174, (1999).

Theodossiou, et al., "The Processing of Plasmid-Based Gene from *E. coli*. Primary Recovery by Filtration," Bioprocess Engineering 16, pp. 175-185, (1997).

Theodossiou, et al., "Methods of Enhancing the Recovery of Plasmid Genes from Neutralized Cell Lysate," Bioprocess Engineering 20, p. 147-156, (1999).

Varley, et al., "Production of Plasmid DNA for Human Gene Therapy Using Modified Alkaline Cell Lysis and Expanded Bed Anion Exchange Chromatography," Bioseparation 8, pp. 209-217, (1999).

"Clearance of Endotoxin from Solution by Absorptive Filtration with Sartobind™ Membrane Absorbers," Sartorious Corporation, Developing Methods #7, Pub No. SL-4034-e97052, (1997).

Zasloff, et al., "A New Method for the Purification and Identification of Covalently Closed Circular DNA Molecules," Nucleic Acids Research 5, pp. 1139-1153, (1978).

Gomez et al., "Determining Equivalent Pore Diameter for Rigid Porous Spargers," The Canadian Journal of Chemical Engineering 78, pp. 785-792, (2000).

Kawagoe, et al., "Liquid-Phase Mass Transfer Coefficient and Bubble Size in Gas Sparged Contractors," Journal of Chemical Engineering of Japan, pp. 254-256 (1975).

Sridhar et al., "Gas Holdup and Bubble Diameters in Pressurized Gas-Liquid Stirred Vessels," Ind. Eng. Chem. Fundam. 19, pp. 21-26, (1980).

Search Report for Application No. 03749647.8-2405 PCT. European Patent Office Nov. 3, 2005.

* cited by examiner

A:

B:

APPARATUS AND METHOD FOR PREPARATIVE SCALE PURIFICATION OF NUCLEIC ACIDS

CROSS-REFERENCE TO RELATED APPLICATIONS

This application is a Divisional Application of, and claims priority to, U.S. patent application Ser. No. 10/527,618, filed Mar. 11, 2005, and issuing as U.S. Pat. No. 7,314,746 on Jan. 1, 2008, which claims priority as a 35 U.S.C. §371 filing to PCT/US2003/028759, filed on Sep. 12, 2003, which claims priority to U.S. Provisional Application 60/410,617, filed Sep. 13, 2002, all of which are incorporated herein by reference.

TECHNICAL FIELD

The invention relates to methods for purifying nucleic acids. The invention relates in particular to methods for preparing pharmaceutical quality plasmid DNA at preparative scale.

BACKGROUND OF THE INVENTION

Since the advent of recombinant DNA, methods have been developed and improved for the purification of DNA and RNA to further molecular biology research. While these methods have allowed considerable study of nucleic acids in research environments, methods for preparative scale production of plasmid DNA sufficient in quantity and quality for clinical use have been problematic and continue to represent an unmet need.

Gene therapy involves the introduction of nucleic acid into a patient's cells, which, when expressed, provide a therapeutic benefit to the patient. Examples include the introduction of an exogenous, functional gene to correct a genetic defect in a patient carrying a defective gene or to compensate for a gene that is not expressed at sufficient levels. Other examples include the introduction of mutant genes, antisense sequences or ribozymes to block a genetic function, e.g., in the treatment of viral infections or cancer.

For any application in which nucleic acid is introduced into a human or animal in a therapeutic context, there is a need to produce highly purified, pharmaceutical grade nucleic acid. Such purified nucleic acid must meet drug quality standards of safety, potency and efficacy. In addition, it is desirable to have a scaleable process that can be used to produce multiple gram quantities of DNA. Thus, it is desirable to have a process for producing highly pure nucleic acid that does not require toxic chemicals, known mutagens, organic solvents, or other reagents that would compromise the safety or efficacy of the resulting nucleic acid, or make scale-up difficult or impractical. It is also desirable to prepare nucleic acids free from contaminating endotoxins, which if administered to a patient could elicit a toxic response. Removal of contaminating endotoxins is particularly important where plasmid or bacteriophage DNA is purified from gram-negative bacterial sources that have high levels of endotoxins as an integral component of the outer cell membrane.

Preparative scale plasmid manufacturing most commonly involves alkaline lysis of bacterial cells containing extrachromosomal DNA of interest such as plasmid or phage DNA. Alkaline lysis was first developed by Birnboim and Doly, Nucleic Acids Res 1979; 7(6):1513-23, as a screening method for recombinant plasmids. As Birnboim and Doly found, alkaline lysis of bacteria effects release of intracellular plasmid DNA together with selective denaturation of chromosomal DNA that renatures upon neutralization to form an insoluble "clot" together with cellular debris. The lysate from an alkaline lysis process, such as for example the method of Birnboim and Doly, usually consists of a slurry of precipitated or flocculated debris suspended in a golden yellow colored liquid. The plasmid DNA remains predominantly in the liquid portion of the neutralized solution. To obtain the liquid containing desired extrachromosomal polynucleotides, the debris has to be removed from the slurry without shearing of either the precipitated chromosomal DNA debris or the extrachromosomal polynucleotide products. As in the minipreparative technique of Birnboim and Doly, centrifugation is the most commonly used method to isolate the liquid from the solid precipitates. On a preparative scale, various means have been employed to clarify the alkaline lysate including centrifugation, sedimentation, and filtration. Centrifugation has been commonly employed. (Bussey et al., U.S. Pat. No. 6,011,148; Butler et al., U.S. Pat. No. 6,313,285). Filtration means have included bag filtration (Thatcher et al., U.S. Pat. No. 5,981,735), depth filtration (Mittelstaedt and Hsu, U.S. Pat. No. 6,268,492) and filtration with diatomaceous earth (Horn et al., U.S. Pat. No. 5,576,196).

While continuous-flow centrifugation can be efficient for the separation, the shearing motion can result in irreversible damage to the plasmid. On the other hand, batch centrifugation involves complete containment of the lysate inside centrifuge bottles, which prevents the degradation during centrifugation. However, scaling up the batch centrifugation process has been constrained by the lack of commercial availability of larger centrifuges. Also, having multiple centrifuges may not be feasible, due to the prohibitive expense. Thus, as the scale of the production run increases, the volume of material makes the traditional centrifugation, sedimentation, and filtration means too inefficient, time consuming and/or expensive. A more efficient method of removing the precipitated debris is therefore needed.

The invention described provides a novel method and apparatus for clarification of cell lysates that is rapid, highly efficient, relatively inexpensive and conducive to automation.

BRIEF SUMMARY OF THE INVENTION

The present invention is directed to a method for purifying nucleic acids from lysed cells that is suitable for preparative scale manufacture. The method and apparatus of the invention provides automatable manufacturing of high quality extrachromosomal nucleic acids, particularly plasmid and phage DNA, from bacterial cells. Extrachromosomal nucleic acids prepared according to the present invention are suitable for clinical use.

The invention provides novel methods and apparatus to separate cell debris precipitates from the liquid phase of cell lysates. In particular, the methods and apparatus of the invention are suitable for generating a clarified bacterial lysate using flotation to separate and eliminate undesired insoluble cellular debris including chromosomal DNA. According to the invention, gas such as for example air or nitrogen, is controllably introduced into a lysis process in order to provide a motive force for phase separation by generating a buoyant flocculent or precipitate phase containing cellular debris that is readily separated from an underlying clarified liquid phase containing extrachromosomal nucleic acids.

In one embodiment, the gas is introduced to controllably generate bubbles that reduce the density of the cell debris and create a buoyant flocculent phase that can be readily separated from, and thus provide, a substantially clarified fluid lysate phase that is enriched in plasmid DNA but substantially depleted of cellular proteins and chromosomal DNA. In one embodiment, the bubbles are controllably introduced and the resultant buoyant flocculent phase is allowed to coalesce and stabilize within a defined period of time, thus permitting defined manufacturing process parameters.

In one embodiment, the gas is controllably introduced through a device that generates gas bubbles of defined size. In one such embodiment, recovery of liquid lysate and the stability of the floating cell debris is improved by adding the gas through an air or "sparge" stone.

In one embodiment, the methods involve a continuous flow in-line process including use of static mixers to mix the cells with a lysis solution to provide controlled, gentle mixing of the cells with the lysis solution. Static mixers are further used to mix the resulting lysis mixture with a precipitation solution to separate out cell debris and other contaminants, including chromosomal DNA.

Liquid phase recovery is maximized by optimizing the flow rates of both air and liquid. In a one embodiment, the recommended conditions for flotation, plasmid yield, and lysate quality through an in-line lysis apparatus using an alkaline lysis procedure were found to be 0.3 ft/s linear velocity with 12% air introduced at the initiation of lysis through a stainless steel sparge stone having about 2 micron holes.

In further embodiments, the clarified lysate is further purified. Optionally a series of filters including depth filters and filters having charge characteristics sufficient to remove certain contaminants are employed. In one embodiment, the clarified lysate of the present invention is passed through depth filters of decreasing pore size, for example an about 8 to about 10 micron depth filter followed in series with an about 2 micron depth filter followed by passage through glass fiber and nylon filters to provide a filtered clarified lysate.

In a further embodiment, the filtered clarified lysate is further purified by ion exchange chromatography to remove residual impurities including cellular proteins, chromosomal DNA, RNA and endotoxins.

The methods of the invention are sufficient to provide a purified DNA solution in a high volume process that does not require a centrifugation step subsequent to cell lysis. The process further does not require complex purification steps (e.g., ultrafiltration) prior to ion exchange chromatography. Optionally the ion exchange-purified material is further subject to an ultrafiltration/diafiltration step.

When desired, the methods can be readily automated according to well-known methods by including appropriate computer controls of steps in the process to ensure desired results. The invention also provides particular conditions by which the methods can be used to prepare extrachromosomal polynucleotide drug products in an automated manner.

DESCRIPTION THE DRAWINGS

Figure 5:
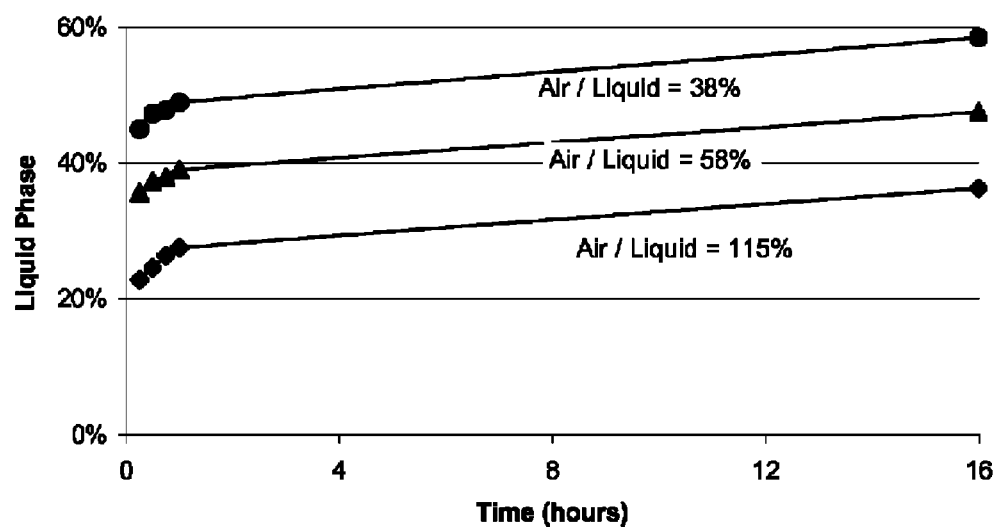
Figure 5:
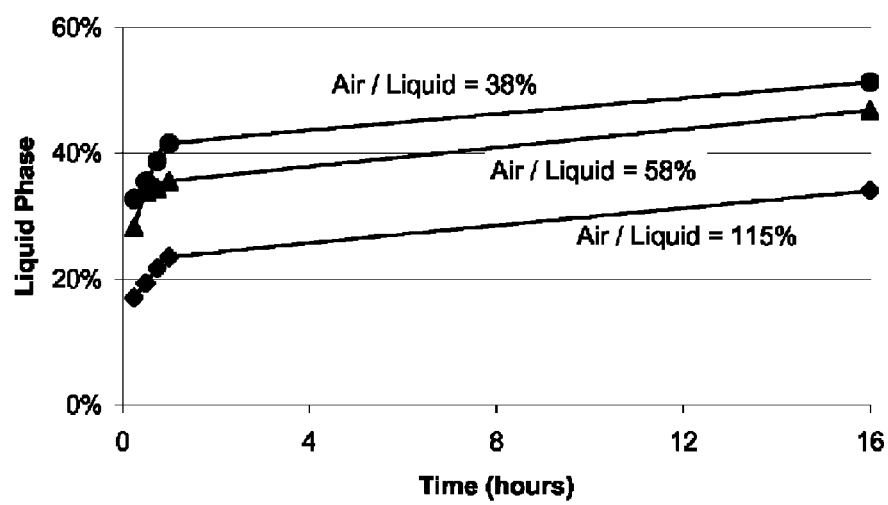

FIGS. 5A and B represent the relative effects of different quantities of gas on the ultimate volume of a resultant liquid phase after separation depending on whether the gas is introduced at the beginning of the lysis procedure compared with entry of gas at the time the precipitation buffer is added. In FIG. 5A the gas is introduced essentially together with the cell lysis buffer. In FIG. 5B the gas is introduced essentially together with the precipitation buffer.

Figure 6:
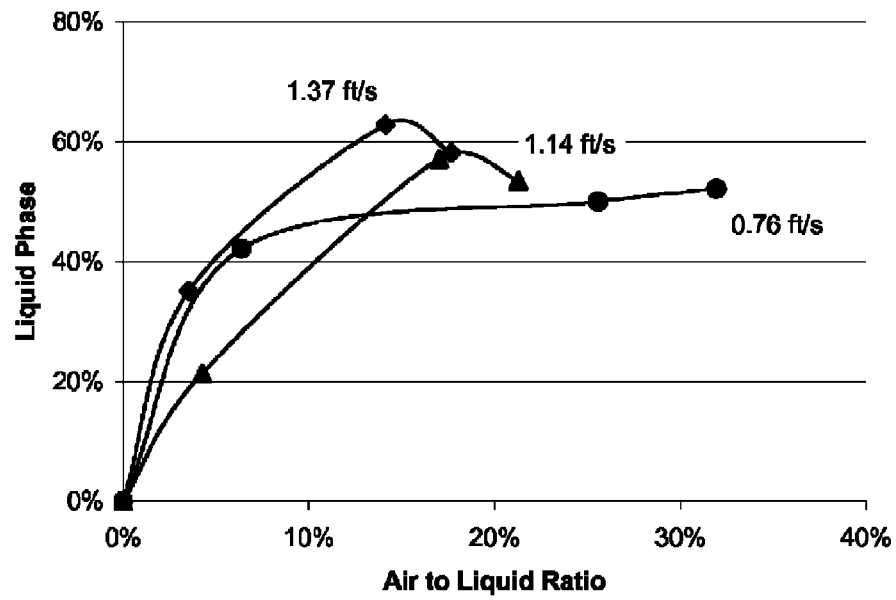

FIG. 6 represents the relative lysate recovery volume after 2 hours of resting flotation depending on different volumes of gas added through a "T" junction at different fluid flow rates.

Figure 7:
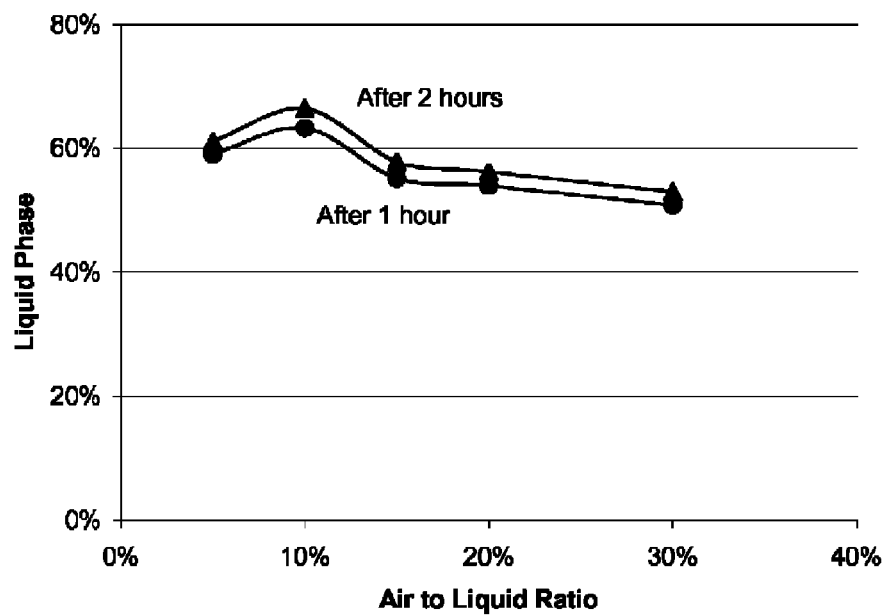

FIG. 7 represents the relative lysate recovery volume after 1 and 2 hours of resting flotation depending the relative effects of different volumes of gas added through a sparge stone.

Figure 8:
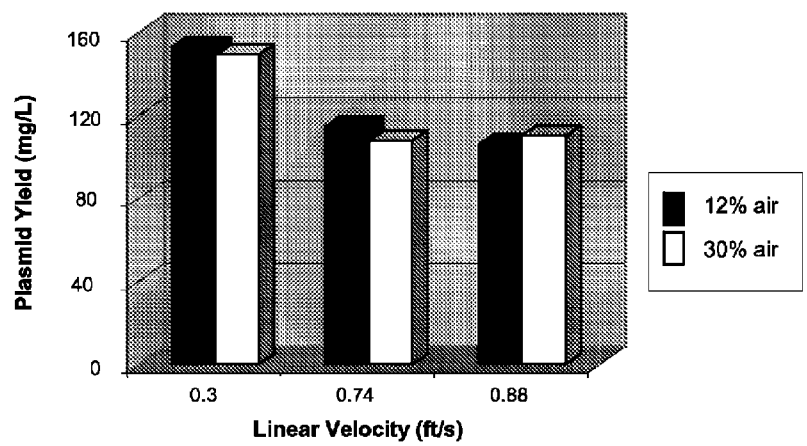

FIG. 8 depicts the effects of linear velocity at different percentage air volumes on plasmid yield.

Figure 9:
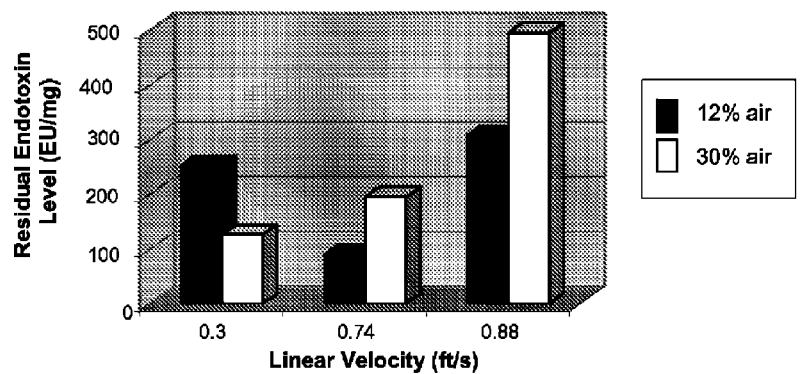

FIG. 9 depicts the effects of linear velocity at different percentage air volumes on residual endotoxin levels.

Figure 10:
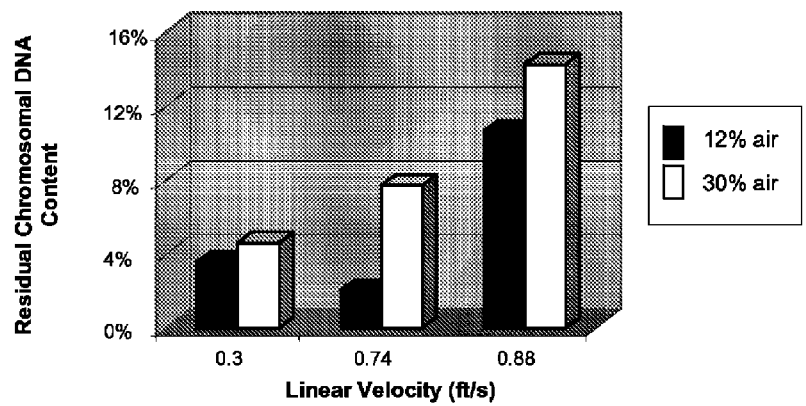

FIG. 10 depicts the effects of linear velocity at different percentage air volumes on residual chromosomal DNA content.

Figure 11:
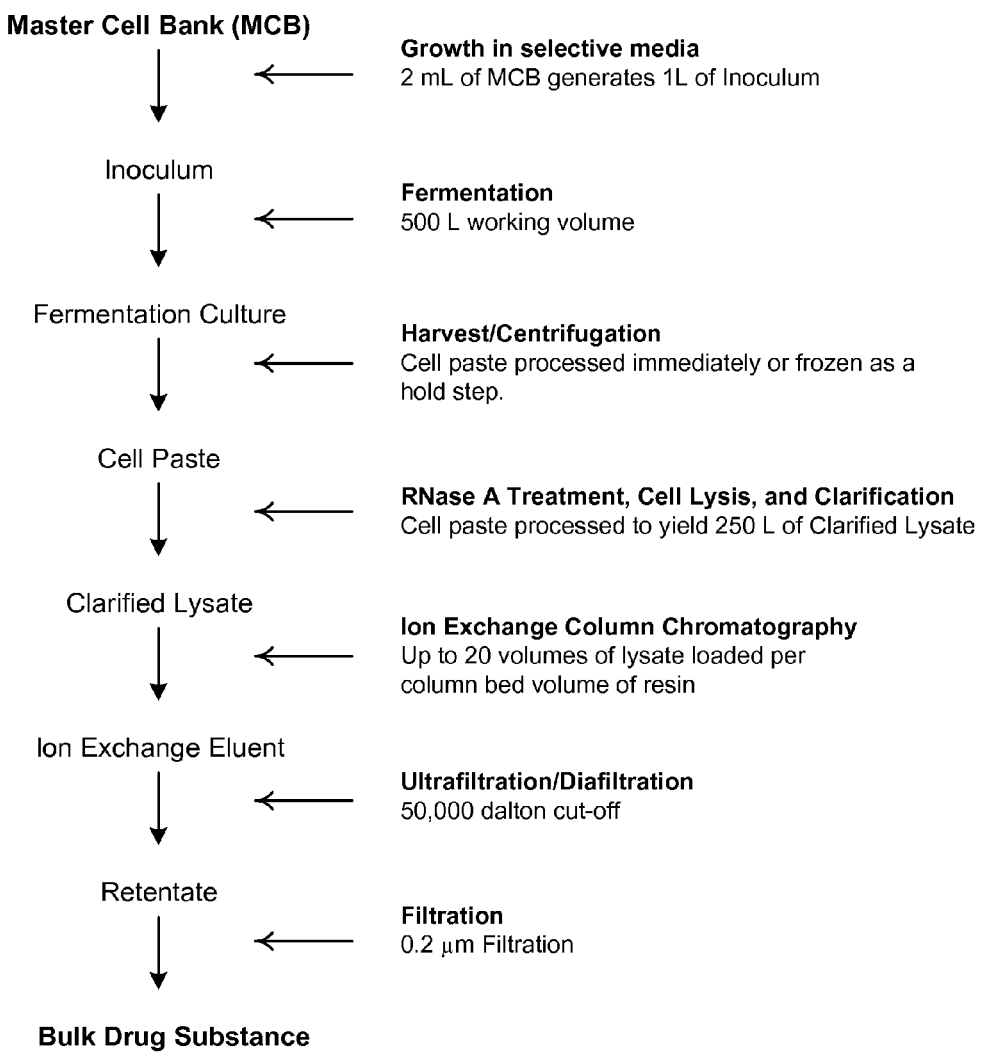

FIG. 11 is a general process flow chart for plasmid purification according to the present invention.

DETAILED DESCRIPTION OF THE INVENTION

The present invention may be utilized in a highly streamlined process for the purification of high quality pharmaceutical grade polynucleotides at a preparative scale. The process minimizes complex or expensive purification steps, thus minimizing cost and allowing an increase in throughput. It is also an advantage of the invention that the process is readily automated and minimizes the use of apparatus that may shear the chromosomal DNA, thus avoiding potential contamination of the extrachromosomal nucleic acid preparation. The process is particularly suitable for providing pharmaceutical grade plasmid and phage DNA at commercial scale from bacterial cell lysates.

The general process sequence for producing pharmaceutical grade plasmid DNA from bacterial cells is depicted in FIG. 11 as follows: 1) inoculation from a master cell bank; 2) fermentation; 3) harvest and production of a cell paste; 4) cell lysis and clarification of the lysate; 5) ion exchange chromatography; 6) ultrafiltration/diafiltration; and 7) final filtration to produce a bulk drug substance.

In one embodiment, an apparatus is provided for producing a clarified bacterial lysate according to the following steps: 1) lysis of a bacterial cell suspension; 2) controlled introduction of a gas sufficient to float a subsequent precipitate/flocculent; 3) introduction of an agent that effects precipitation/flocculation of cell debris from the lysed bacterial cells; and 4) separation of the precipitate/flocculent resulting in isolation of a clarified lysate.

For purposes of the present invention, the term "precipitate" means no longer soluble or in solution. As such, the terms "precipitate" and "flocculent" are used interchangeably herein to refer to the formation of essentially insoluble clumps of cellular debris, including cell wall constituents, chromosomal DNA and protein, that form as a consequence of the lysis of live cells and chemical treatment of such lysate. The present inventors found that portions of the "flocculent" tended to float and devised apparatus and methods that result in flotation of a majority of the visual precipitate thus resulting in highly effective phase separation from a resulting clear fluid phase containing the extrachromosomal nucleic acid product of the fermentation.

In one embodiment, gas in the form of compressed air, or alternatively nitrogen or other pharmaceutically acceptable gas or mixture of gases, is controllably introduced into an aqueous lysis mixture in order to controllably form bubbles that effect flotation of cellular debris precipitates resulting from chemical treatment of the lysate. Gas can be introduced into the process through any means that is amenable to control of the volume of gas introduced and through which bubbles can be controllably formed in a lysis solution. Thus, it is desirable to have flow control means for the introduction of the gas. Gas can be introduced through any port including for example "T" junctions, perforated rigid or flexible tubing, or injection ports and may further include means for the generation of small bubbles such as, for example, air or "sparge" stones or perforated filter disks.

In a preferred embodiment, the size of gas bubble produced is controlled by introducing the gas through an aperture having a multiplicity of small holes, preferably of relatively uniform size. In this embodiment, any apparatus able to generate small bubbles, such as for example sintered glass disks, disc filters or aeration stones or sparge stones formed of glass, plastic, or metal, may be employed. For purposes of the present invention the term "sparge stone" refers to any perforated means through which gas can be introduced into the liquid lysis milieu and form small bubbles. In one embodiment, a sparge stone is placed in the input line for an alkaline lysis buffer. The sparge stone should be composed of a material that is non reactive with the lysis milieu. The apparatus may be composed of a material that can be cleaned and reused or may be disposable.

In one embodiment, the gas is introduced into the lysis milieu through a stainless steel sparge stone. Inert metal sparge stones may be used repeatedly and may be cleaned by acid/base washes and sterilized by autoclaving. In a preferred embodiment, the sparge stone is oriented vertically in the fluid flow path in such a way that the bubbles formed are allowed to rise directly up into the fluid stream.

In one embodiment, a sparge stone is employed having small holes or pores of a relatively uniform diameter. In one embodiment the pores have an average diameter of less than about 5 microns in diameter. In one preferred embodiment, a stainless steel sparge stone having uniform pores of approximately 2 microns in diameter is employed resulting in the formation of uniform small bubbles and an overall volume of gas of approximately 12% of the total volume. Large bubbles, if desired, may require adjustment to the use of larger gas volumes. Larger bubbles may require a faster flow rate in order to accommodate the volume of gas and result in greater trapping of fluid in the floating layer ultimately formed.

In one embodiment, the unclarified lysate is allowed to separate from the cell debris precipitate/flocculent, including introduced bubbles, for approximately 1 to 2 hours at ambient temperature. The precipitate floats to the top of the tank due to the air bubbles introduced into the mixture. Typically, the controlled introduction of gas into the procedure permits in immediate phase separation of a buoyant flocculent phase following addition of the precipitation buffer. However, in one embodiment the mixture is allowed to rest in a tank for approximately 1 to 2 hours in order for the buoyant flocculent to coalesce and solidify prior to removal of the clear clarified lysate phase from under the buoyant precipitate/flocculent phase. The configuration of the lysate tank is modified depending on the volume of material to be separated. Thus, even small volumes may be effectively separated using a tall, narrow tank. Surprisingly, in large volume lysis the separation effected through flotation of the precipitate allows for isolation of a clarified lysate in 1 to 2 hours that is superior to that obtained with over 8 hours of centrifugation.

Figure 4:
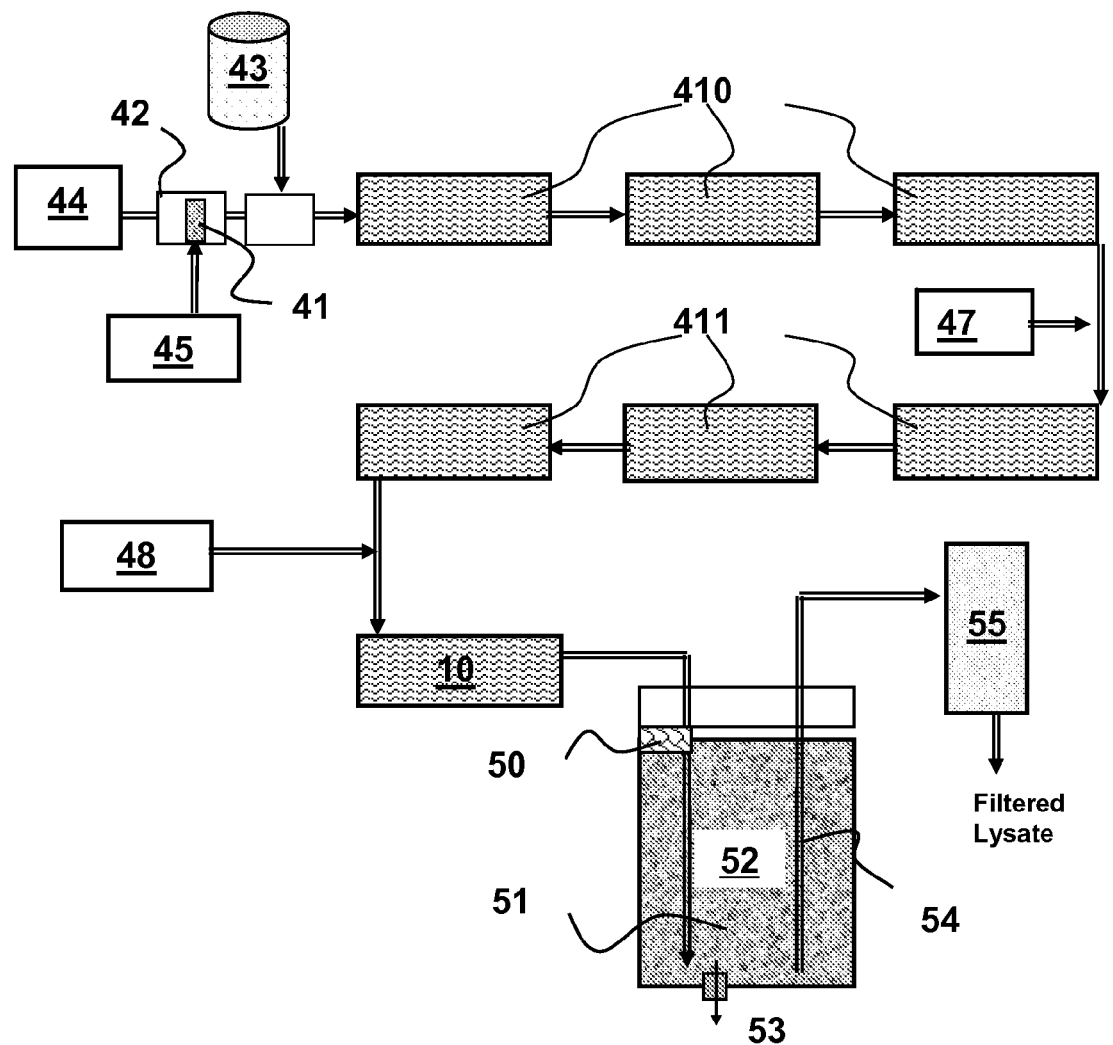
FIG. 4 illustrates a schematic diagram of an in-line bacterial cell lysis apparatus in accordance with the present invention.

In one embodiment, a continuous flow in-line apparatus is provided for producing a clarified bacterial lysate by conducting the following steps in accordance with FIG. 4: 1) in-line chemical lysis of a bacterial cell suspension in conjunction with controlled introduction of a gas sufficient to float a subsequent precipitate/flocculent; 2) in-line precipitation/flocculation of cell debris from the lysed bacterial cells; and 3) separation of the floating precipitate/flocculent phase from a resulting clarified lysate phase. FIG. 4 presents an embodiment including a step of adjusting the pH of the lysate before separation of the precipitate/flocculent to protect the DNA from depurination and to generate a clarified or filtered lysate that may be directly applied to an ion exchange step. Alternatively, if the lysis and precipitation conditions result in an essentially neutral pH, addition of a further pH adjustment buffer may be avoided. Thus, in one embodiment the pH adjustment step is considered optional depending on the lysis/precipitation conditions.

In one embodiment the process involves a lysis procedure including a surfactant that enhances the formation of a buoyant flocculent upon addition of a compound that induces precipitation/flocculation of chromosomal DNA and cellular debris from the lysed cells.

In one embodiment, apparatus and methods are provided for alkaline lysis in which bacterial cells from a previously collected cell paste are resuspended in 25 mM Tris, 10 mM $Na_2EDTA$, 83 mM Dextrose pH 8.50 at a ratio of 5 liters per kilogram of cell paste. The resuspended cells are then introduced into a in-line continuous flow apparatus wherein they are lysed with an alkaline lysis buffer (0.2M NaOH, 1% SDS; approximately 10 liters per original kilogram (kg) of cell paste) in conjunction with controlled introduction of a gas sufficient to float a subsequent precipitate/flocculent, followed by in-line precipitation/flocculation using 3 M potassium acetate/2M acetic acid, pH 5 (5 liters per kg of cell paste). A further pH adjustment buffer (2.5 M Tris, pH 8.5, 4-5 liters per kilogram of paste) is added in-line prior to flotation of the precipitate/flocculent.

In one embodiment, RNase is added to digest RNA released by the cells after lysis. For example, in one embodiment 5 mL of RNase A per kg of cell paste (approximately 15,000-24,000 Kunitz units/kg) is added to digest RNA and the cell suspension is mixed for 1-2 hours at ambient temperature using bow-tie impeller prior to in-line lysis. Alternatively, methods may be employed to reduce or eliminate the bacterial RNA without using RNase. For example, prolongation of the alkaline lysis step for 4 to 24 hours together with the addition of lysozyme has been employed to reduce the levels of RNase. (Butler et al., U.S. Pat. No. 6,313,285). Alternately, residual RNA and chromosomal DNA can be reduced by ammonium sulfate precipitation following alkaline lysis, precipitation, and clarification. (McNeilly et al., U.S. Pat. No. 6,214,586). Other methods that may be employed include the use of bacterial strains in which a gene encoding RNase is stably introduced into the bacterial host genome or transiently expressed via a plasmid. Expression of the RNase gene is induced near the end of fermentation in order to produce a local source of the RNase enzyme.

"Extrachromosomal nucleic acids" include DNA, RNA and chimeric DNA/RNA molecules that do not constitute the primary genome of eukaryotic or prokaryotic host cells. Nucleic acids that may be purified include ribosomal RNA, mRNA, snRNAs, tRNA, plasmid DNA, viral RNA or DNA. The present method is particularly suitable for the purification of extrachromosomal phage and plasmid DNAs from prokaryotic cells. Of particular interest are plasmid DNAs encoding therapeutic genes. By "therapeutic genes" is intended to include functional genes or gene fragments which can be expressed in a suitable host cell to complement a defective or under-expressed gene in the host cell, as well as genes or gene fragments that, when expressed, inhibit or suppress the function of a gene in the host cell including, e.g., antisense sequences, ribozymes, transdominant inhibitors, and the like. Plasmid DNA isolated from prokaryotic cells include naturally occurring plasmids as well as recombinant plasmids encoding a gene of interest including, e.g., marker genes or therapeutic genes.

The term "static mixer' refers to any flow-through device that provides enough contact time between two or more liquids to allow substantially complete mixing of the liquids. In the methods of the invention, static mixers are used to mix certain solutions, particularly where gentle and complete mixing is desired. Typically, static mixers contain an internal helical structure which allows the liquids to come in contact in an opposing rotational flow and causes them to mix in a turbulent or laminar flow. Such mixers are described, for instance, in U.S. Pat. No. 3,286,922. Such devices are useful, for instance, in isolating plasmid DNA from lysed bacterial cells, or for precipitating cell debris, proteins, and chromosomal DNA after lysis, as described, for instance, in Christopher et al., U.S. Pat. No. 5,837,529. During these procedures, the mixing should be complete to maximize recovery and should be relatively quick to maintain DNA integrity. If mixing is too vigorous, however, genomic DNA can be sheared and may contaminate the extrachromosomal polynucleotide preparation. Static mixers are advantageous in these applications because substantially complete mixing can be obtained while minimizing shear of genomic DNA. In addition, lysis is typically carried out in caustic solutions such as alkali, which can affect the quality of the final preparation. Since static mixers allow continuous flow, the time in contact with these solutions can be carefully controlled.

The degree of mixing is controlled by varying the linear velocity or flow rate of the solution through the mixer, the type of mixer used, the diameter of the mixer, and the number of elements in the mixer. For instance, in the preparation of plasmid DNA from bacterial cells a laminar flow static mixing environment is preferred such can be obtained at certain flow rates with commercially available static mixers such as for example KENICS brand sanitary mixers available from Chemineer, Inc. The linear velocity used depends on the manufacturer and type of mixer; this controls the Reynolds number achieved and how gentle the mixing is.

A linear velocity of 0.3 to 1.1 feet per second gives acceptable product quality when using a 2" diameter, 36-element, laminar flow static mixer (obtainable for example by placing three 12 element static mixers in-line, i.e. KENICS 2 KMR-SAN 12 sanitary mixers, each individual 12 element mixer having an overall length of 38 inches) with an overall length of about 9 feet corresponding to a Reynolds number from 14 to 53 (calculating the Reynolds based on a 2" diameter (1⅞" i.d.), assuming viscosity=300 cp.). This linear velocity range permits sufficient mixing to thoroughly lyse the cells and yet not be so high that genomic DNA is sheared to a size that is problematic in later purification steps. At a 0.7 feet per second linear velocity the flow rate in a 2" diameter mixer is typically ~22 liters per minute. The flow rate out of the $1^{st}$ mixer will be 22.8 L/min at the indicated linear velocity and size of static mixer. The flow rate would be 30 L/min out of the $2^{nd}$ mixer due to the increase in volume.

The term "continuous flow" or "continuous flow in-line fluid path" refers to an apparatus and system in which an apparatus provides the capability to operate a constant flow process in a contained closed path without discontinuous interruption. It is an advantage of the present invention that cell lysis, precipitation and clarification can be performed in a continuous, automated process by use of static mixers with appropriate adjustment of flow rates. The flow rate must be sufficient to achieve adequate lysis, precipitation and neutralization, but not resulting in shearing of genomic DNA. Appropriate sizing of the static mixers, pumps, flocculent separation apparatus, and selection of flow rate will allow continuous operation of the process, while maximizing yield and quality. Preferably, the process is automated to ensure reproducibility.

The term "precipitation buffer" is used to describe a solution that is used to precipitate proteins, chromosomal DNA and cell debris. When referring to an alkaline lysis procedure, the precipitation buffer may also be termed a neutralization buffer as the precipitation occurs as a result of neutralization of the alkaline lysate. Typically, for an alkaline lysis utilizing 0.2 M NaOH and 1% SDS, the precipitation solution will contain potassium acetate. A suitable precipitating solution is 3M potassium acetate, adjusted to pH 5.5, with 2M acetic acid (~5M acetate final). When utilizing a static mixer, linear velocities are used that ensure sufficient mixing to thoroughly precipitate the proteins and cellular debris and yet are not so high that genomic DNA is sheared to a size that is problematic in later purification steps. Typically, approximately 4.5 liters of precipitating solution are used per kg of cell paste.

The term "pH adjustment buffer" is used to describe a solution that is used to raise the pH of cell lysate after addition of the precipitation solution in order to minimize acid catalyzed de-purination of the DNA and to condition the material for binding onto the anion exchange column, e.g., a pH is the range of 6 to 9, preferably from 7 to 8.5. A useful buffer solution for this purpose is 2.5 M Tris (~pH 11). In one embodiment, the pH adjustment solution is added prior to separation of the buoyant flocculent in order to avoid disruption of the flocculent.

In a further embodiment, an apparatus and system is provided for producing a clarified bacterial lysate in accordance with the following steps: 1) lysis of a bacterial cell suspension in conjunction with controlled introduction of a gas sufficient to float a subsequent precipitate/flocculent; 2) introduction of an agent that effects precipitation/flocculation of cell debris from the lysed bacterial cells; 3) separation of the floating precipitate/flocculent phase from a resulting clarified lysate phase; 4) filtration of the clarified lysate; 5) ion exchange chromatography of the filtered lysate; 6) ultrafiltration/diafiltration of the ion exchange eluate; and 7) final filtration to produce a bulk drug substance.

The following examples illustrate certain aspects of the above-described method and advantageous results. The following examples are shown by way of illustration and not by way of limitation.

EXAMPLE 1: In one embodiment, bacterial cells are lysed by contact with a strongly alkaline solution in the presence of a detergent. A typical alkaline lysis solution is 0.2N sodium hydroxide (NaOH) with 1% sodium dodecyl sulfate (SDS). The classical alkaline lysis procedure of Bimboim and Doly involved lysis of bacteria on a mini-preparative scale in which alkaline conditions effected selective denaturation of chromosomal DNA that renatured upon neutralization and, together with cellular proteins and debris, formed an insoluble "clot" that could be removed by centrifugation. The neutralization step has been also termed "precipitation" for the formation of the insoluble "precipitate." The plasmid DNA remains in the fluid phase of the "neutralized" solution. On a preparative scale, various means have been employed to clarify the alkaline lysate including centrifugation, sedimentation, and filtration. Filtration means have included depth filtration (U.S. Pat. No. 6,268,492) and filtration with diatomaceous earth (U.S. Pat. No. 5,576,196). However, as the scale of the production run increases, the volume of material makes the traditional centrifugation, sedimentation, and filtration means too inefficient, time consuming or expensive. Furthermore, the alkaline lysis "precipitate" might be better described as a "flocculent" in which insoluble material is produced but does not necessarily rapidly settle out of solution.

In one determination of the density of constituents of the lysate by the present inventors, the density of the cell debris was determined to be approximately 1.15 g/mL while the liquid phase was 1.07 g/mL. Based on the difference between the specific gravity of these two phases, cell debris should fall out of solution. However, in practice this is not always the case. Several different conditions of lysates coming out of the static mixers have included those having both floating and sinking precipitates, those having largely suspended precipitates and those having a large component of floating "precipitate."

Regardless of the initial appearance of the lysate exiting the static mixers, the precipitates can typically be induced to form a pellet with sufficient centrifugation. However, prolonged centrifugation may be required for clarification of large preparative scale volumes and it was observed that such centrifugation could result in shearing of the chromosomal DNA and contamination of the plasmid DNA with fragments of chromosomal DNA.

Upon close visual examination, it was found that small air bubbles are present in the solid precipitates that initially float. Based on this observation, a theory was developed that the air trapped in the cell debris may be utilized to provide a buoyancy force needed to counter the higher density of the precipitates. According to this theory, the cell debris could be substantially suspended, or floated, in the lysate if a critical amount of gas could be introduced.

Thus, in development of the present invention, efforts were undertaken to devise new methods and apparatus for separating the precipitate based on inducing the precipitate to float instead of attempting to remove the precipitate by centrifugation or various filtration means. It was surprisingly found that controlled introduction of air into the lysis milieu was able to permit flotation of virtually the entire precipitate/flocculent resulting in high yield recovery of a high quality substantially clarified lysate.

Based on visual observation, most air bubbles that formed the meta-stable cell-debris/air complexes were less than 1 mm in diameter. It was hoped that the efficiency of the formation of such complexes could be improved with optimized air bubble production in the context of the entire lysis procedure.

EXAMPLE 2: Initial Testing: Location of air introduction: During lysis using the static mixer assembly, air was introduced via a separate peristaltic pump into a 3/8" i.d. static mixer arrangement as diagrammatically depicted in FIG. 2. Inside each of Static Mixers 210 and 211 are 36 alternating twisted elements that facilitate better mixing (each of Static Mixers 210 and 211 are formed by connecting in series 3 individual 12 element mixers: 1/2 inch o.d. KENICS 1/2 KMR-SAN 12 sanitary mixers obtainable from Chemineer, Inc.). The flow rates for cell re-suspension 23 (*E. coli* transformed with plasmid pMB290, OD 150), cell lysis buffer 24 (0.2N NaOH; 1% SDS), precipitation buffer 27 (3M KOAc; 2M HOAc) and neutralization buffer 28 (2.5M Tris-base) were 370, 620, 310, and 265 mL/min, respectively. The air was introduced at two alternative locations 5 or 6 via a "T" connection into the static mixer assembly. For each inlet, three settings (600, 900, 1800 mL/min) of air were tested. The separation between the liquid (clarified lysate) and solid (cell debris) phases in lysate 29 was recorded as a function of time. Cell lysis with no air introduction was also run as a control. Table 1 below indicates the tested flow rates in ml/minute for the cell resuspension, and cell lysis precipitation and neutralization buffers.

TABLE 1

Liquid Flow Rates for 3/8" Static Mixers

| Flow Rates in mL/min | Linear Velocity in Static Mixer #1 | | |
|---|---|---|---|
| | 0.76 ft/s | 1.14 ft/s | 1.37 ft/s |
| Cell Re-suspension | 370 | 560 | 670 |
| Cell Lysis Buffer | 620 | 930 | 1120 |
| Cell Precipitation Buffer | 310 | 465 | 560 |
| Neutralization Buffer | 265 | 400 | 480 |

Determination of Location for Introduction of Air: A total of six lysates were generated from the static mixers, with air introduced at either inlet. All six samples were found to contain floating precipitates. However, the degree of compaction of the precipitates was not identical for all samples. During the first hour, the interface continued to rise up to 24-49%. After 16 hours, the liquid phase occupied 34-58%, depending on the airflow rate and location of the inlet. The control sample was found to be a suspension of precipitates that did not clarify by phase separation. The progress of precipitate compaction over time is summarized in FIGS. 5A & 5B.

Figure 2:
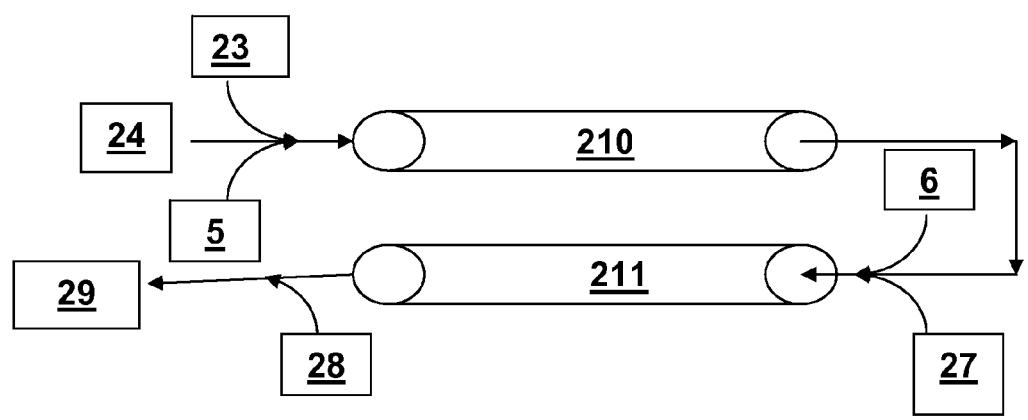
FIG. 2 represents several examples of locations tested for introduction of gas into an inline lysis apparatus and process.

In FIG. 5A, air was delivered through a "T" located prior to the first static mixer in the flow path, as depicted at position 5 in FIG. 2. In FIG. 5B, air was delivered through a "T" located prior to the second static mixer in the flow path, as depicted at position 6 in FIG. 2. The percentages shown on FIGS. 5A and 5B represent a ratio of the flow rate of air to the combined flow rates of all lysate constituents including the flow rates for the cell re-suspension (370 ml/min), cell lysis buffer (620 mL/min), cell precipitation buffer (310 mL/min) and neutralization buffer (265 mL/min). Thus, in both FIGS. 5A and 5B, the circles represent an air/lysate ratio of 38% (600 ml per min air/1565 ml per min combined lysate flow), the triangles represent an air/liquid ratio of 58% (900 ml per min air/1565 ml per min combined lysate flow) and the diamonds represent an air to lysate ratio of 115% (1800 ml per min air/1565 ml per min combined lysate flow).

Comparing the data in each figure, it was found that better recovery was achieved when air was introduced prior to the first static mixer. The air delivered through the "T" creates primarily air pockets. The fine air bubbles (<1 mm) required for flotation are thought to be generated by the turbulent mixing action inside the static mixers. Therefore, flotation is enhanced when air is introduced at the front end of the static mixers rather than the middle.

Air Flow Rate Determination: A second set of experiments was designed to determine the relationship between the liquid and air flow rates for flotation. In this experiment, combinations of three liquid linear velocities and three air flow rates were tested on the same 3/8" static mixer used in the first experiment. Liquid flow rates were maintained by peristaltic pumps at the settings shown in Table 1. Linear velocities shown in Table 1 were calculated based on empty cylindrical tubes without air introduction. Air flow was controlled by a mass flow controller (Cole-Palmer, Model P-33115-60) at 100-500 mL/min.

The best separation occurred at the lowest airflow rate among the three settings tested. However, the optimal amount of air may be lower than this flow rate based on extrapolation of the results. With high air flow rates, the excess air introduced into the static mixers created foaming that served to increase the total volume of the floating precipitate. As a result, the recovery of liquid as a percentage was negatively affected.

Most of the compaction occurred during the initial hour after cell lysis. After 16 hours of settling, small amount of precipitate began to fall to the bottom of the containers. Sinking precipitate can pose a problem, such as fouling for the subsequent filtration step, indicating that unclarified lysate, i.e. where the liquid phase has not been removed from the flocculent phase, should not be allowed to stand indefinitely.

Determination of Optimal Flow Rates through a "T": The previous set of experiments served to define the effective location of air entering the static mixers. The present set of experiments were designed to optimize the amount of air required for flotation. Since the floating and sinking behavior of the precipitates is dependent on the formation of the metastable complex between the irregularly shaped cell debris and air bubbles, both the amount of air in the system and the size of the cell debris should be optimized simultaneously to produce the best result. One of the most critical parameters for controlling the size of the cell debris is the linear velocity of the fluid stream. Changes in the ratio and concentration of each buffer should be optimized for efficiency of lysis with optimization of total flow rate where the size of cell debris is the parameter to be influenced. High linear velocity inside the static mixer increases the shear rate, which affects the size of cell debris and air bubbles.

In this set of experiments, a total of ten lysate samples were generated, including a control sample with no addition of air. These lysates were allowed to settle while the upward movement of the lysate-precipitate interface was tracked. After two hours of settling, when the rate of compaction slowed, recoveries of lysates were recorded. FIG. 6 shows the relationship between flotation, linear velocity, and airflow rates.

As demonstrated in FIG. 6, different maximal values of air-to-liquid ratio were found for different linear velocities in the static mixers. A trend of better recovery for high linear velocities at lower air-to-liquid ratio was observed. The trend may be best explained by the reasoning that air bubbles are sheared to finer size at higher linear velocity. The drag force per unit volume is inversely proportional to the diameter of the bubbles. With larger drag force acting against them, smaller air bubbles generated at high linear velocity actually move slower and stay in the lysate solution longer, which may facilitate formation of the precipitate/air bubble complex necessary for flotation.

Figure 1:
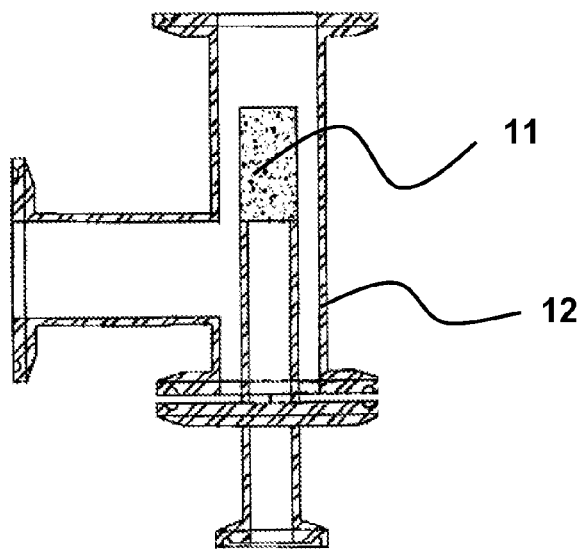
FIG. 1 illustrates a sparge stone assembly according to one embodiment of the present invention.

EXAMPLE 3: Sparge Stone Development: A set of experiments was run on a ⅝" i.d. static mixer setup similar to the arrangement shown in FIG. 2 (each of Static Mixers 210 and 211 are formed by connecting in series 3 individual 12 element mixers: ¾ inch o.d. KENICS ¾ KMR-SAN 12 sanitary mixers obtainable from Chemineer, Inc.). In this experiment, air was delivered into the static mixers by means of a stainless steel "sparge stone" located at first Air Inlet 5. A schematic diagram of one embodiment of a sparge stone including optional housing is shown in FIG. 1. Referring to FIG. 1, sparge stone 11 features 2 micron pores to produce air bubbles less than 1 mm in diameter. During operation, cell lysis buffer enters from one port of housing 12 and completely fills the interior space. Air is controllably introduced through a bottom port of housing 12 under pressure and enters the lysate stream through the sparge stone 11 to produce fine bubbles in the lysate stream. The airflow rate was controlled at 0.25-1.5 L/min by a mass flow controller. Buffer flow rates were set at 1.2, 2.0, 1.0, and 0.85 L/min, respectively, for the four buffers during cell lysis. The compaction of floating precipitates was monitored for up to 2 hours. The same experiment was repeated with the "T" instead of the sparge stone for comparison.

Determination of Optimal Air Flow Rates through "Sparge Stone": Having concluded that air bubbles, especially those with small diameter, seem to be the major determining factor for flotation of precipitates, a more efficient method of generating the bubbles was sought. In light of results from previous experiments, a sparge stone made with stainless steel was designed with such intent. The sparge stone, which was installed at the front end of the static mixers, features pores that generate air bubbles of <1 mm in diameter at flow rate of up to 5 L/min. The flow rate was controlled by a mass flow controller placed upstream of the sparge stone. In this set of experiments, the buffer flow rates are fixed, producing a linear velocity inside the first mixer of 0.88 ft/s. Based on the results from previous experiment using addition of air through the "T", the optimal flotation condition was expected to be achieved with airflow rate equivalent to less than 20% of the total liquid flow rate. The liquid phase recoveries for several air-to-liquid ratios are shown in FIG. 7.

As shown in FIG. 7, the optimal condition was found at ~10% air-to-liquid ratio. Note that the requirement for air is much lower than previous experiments where air was introduced through a "T." Moreover, the extent of compaction of the floating precipitate at a given time was found to be slightly better than the previous experiments. In general, by using the sparge stone instead of the "T", better liquid phase recovery was achieved with less air and lower linear velocity.

EXAMPLE 4: Effect of Flotation on pDNA Quality: A set of experiments was focused on examining the effect of the flotation method on the quality of the plasmid. The ⅝" static mixers were set up with the sparge stone as in the previous set of experiments. Cell lysis was repeated using three linear velocities as per Table 2 while air was delivered through the sparge stone at either 12% or 30% of the total flow rate.

TABLE 2

Liquid Flow Rates for ⅝" Static Mixers

| Flow Rates in mL/min | Linear Velocity in Static Mixer #1 | | |
| --- | --- | --- | --- |
| | 0.30 ft/s | 0.74 ft/s | 0.88 ft/s |
| Cell Re-suspension | 410 | 1000 | 1200 |
| Cell Lysis Buffer | 680 | 1670 | 1990 |
| Cell Precipitation Buffer | 340 | 840 | 1000 |
| Neutralization Buffer | 290 | 720 | 850 |

The lysates were centrifuged after cell lysis and subsequently filtered through 1.2 micron GF2 and 0.2 micron ULTIPORE N66 capsules. At that point, the plasmid concentration in each lysate was determined by HPLC. Each clarified lysate was then loaded onto a column packed with TMAE anion exchange resin for purification. Column eluates (purified pDNA) were analyzed for residual host DNA (genomic DNA) concentration. Samples were assayed for genomic DNA using a slot blot assay, except that the arrangement of samples and sample dilutions on the blot were changed to maximize the number of samples assayed on each blot.

Effect of Linear Velocity and Air Flow Rate on the Quality of Plasmids: It is well known that DNA is a delicate macromolecule that is shear-sensitive. The question arose whether the high liquid and air flow rates required for flotation might inflict damage on the pDNA such as conversion from supercoiled to open-circular, or lead to breakage of genomic DNA into fragments, which would be difficult to separate from the pDNA in subsequent steps. In this set of experiments, alkaline cell lysis was run at several combinations of liquid and airflow rates. Plasmid yield for these lysates is shown in FIG. 8.

Plasmid yield showed a declining trend when the linear velocity (in the first mixer) increased from 0.3 to 0.88 ft/s. The drop in plasmid yield might be explained as insufficient contact time between the cells and the lysis solution in the first mixer. On the other hand, differences in the amount of air addition have minimal effect on the plasmid yield. However, if excessive amounts of air were introduced into the static mixer, efficiency of cell lysis would likely be reduced as air might prevent contact between the cells and the lysis buffer.

The lysates produced in these experiments were further processed by filtration and anion exchange column chromatography. Comparisons between the residual endotoxin and chromosomal DNA content in column eluates are shown in FIGS. 9 & 10. As shown in FIGS. 9 and 10, higher residual content of both endotoxin and chromosomal DNA were found in the purified pDNA from lysates produced at faster flow rates. High linear velocity in the static mixers translates to higher shear rate for all the components in the lysates, and macromolecules are extremely sensitive to shear rate. At higher flow rates, it appears that more residual cell debris was sheared to comparable size of the plasmid, and became inseparable from the pDNA by the subsequent processing steps.

The floating and sinking behavior of cell debris was characterized by a model based on the change in density of the two phases in the lysate. Fine air bubbles with less than 1 mm in diameter provided superior flotation of cell debris. It was observed that the flotation of cell debris is affected by the flow rates of both air and buffers. In addition, both plasmid yield and quality of lysate were determined to decrease with higher linear velocity in the static mixers. Based on the findings of this study, the preferred conditions for flotation of cell debris from the lysate were determined to be: linear velocity maintained at 0.3 ft/s with 12% air introduced through a "sparge stone" device placed in-line with the cell lysis buffer conduit prior to entry of the cell suspension and before a first set of static mixers.

EXAMPLE 5: Fermentation and cell paste: In one embodiment, plasmids having the pUC ori are employed in DH5α *Escherichia coli* (*E. coli*) hosts. The inoculum is prepared from the Master Cell Bank using a target density of $2-6\times10^7$ colony forming units per milliliter ("cfu/mL"). The cells are grown in a shake flask under the selective pressure of 50 micrograms/milliliter (micrograms/ml) kanamycin. After reaching $2-6\times10^7$ cfu/mL, the inoculum is used to seed the bioreactor, or the material may be held for not longer than 8 hours at 2-8° C. prior to further processing.

The inoculum is seeded into the bioreactor at a density of $>1.0\times10^6$ colony forming units/milliliter (cfu/ml). Where the plasmid has an antibiotic resistant gene such as for example KanR, the cells are grown under the selective pressure of 50 micrograms/mL kanamycin. Alternatively, the plasmid copy number may be regulated by conferring other beneficial traits known to those of skill in the art. For example, plasmid copy number may be increased utilizing repressor titration in accordance with U.S. Pat. No. 6,103,470, incorporated herein by reference.

A polypropyleneoxide-polyethyleneoxide block polymer may be added to control foaming. The pH is controlled by sulfuric acid and sodium hydroxide. The temperature and dissolved oxygen are also controlled. The batch fermentation is halted when the cells exhaust nutrients (typically 18 to 22 hours later) and the culture is cooled and harvested. Fermentation end point is based on the off gas $CO_2$ levels representing a spike in acid & base utilization.

The fermentor culture is cooled to approximately 15° C. and harvested using a centrifuge at approximately 15,000 rpm to generate a cell paste that is 45-50% wet weight. The cell paste is processed immediately, or it may be stored at $\leq-60°$ C. for up to 3 years prior to further processing. The weight of cell paste determines the volumes of the subsequent steps.

Cell Resuspension: If frozen, the frozen cell paste was broken by a plastic mallet into pieces of <2×2 centimeters (cm) or pelletized by a mill. Broken cell paste was suspended in Resuspension buffer (25 mM Tris, 10 mM $Na_2EDTA$, 50-83 mM dextrose pH 8.50, dextrose is added only if the paste has been frozen) at a ratio of 5 liters per kilogram of cell paste and maintained between 10-25° C. During paste addition, the cell suspension is gently mixed with a bow-tie impeller at approximately 200-400 rpm, typically for less than 1 hour although other suitable means of mixing can be employed. The optical density of the cell suspension should be less than or equal to 100 $OD_{600}$ for efficient lysis and recovery of plasmid DNA ("pDNA"). In this example, 5 mL of RNase A per kg of cell paste (approximately 15,000-24,000 Kunitz units/kg) is added to digest RNA and the cell suspension is mixed for about 1 to 2 hours at ambient temperature using bow-tie impeller prior to in-line lysis.

The $OD_{600}$ is measured. If the $OD_{600}$ is >100, the cell paste solution is diluted with Resuspension Buffer until the $OD_{600}$ less than or equal to 100 and mixed thoroughly for at least 5 minutes after buffer addition. The pH is adjusted to 8.0±0.5 with 2.5 M Tris buffer and mixed thoroughly for at least 5 minutes after buffer addition. The resulting cell suspension is then subject to lysis.

Continuous Flow In-Line Processing: Following cell suspension, the process is preferably conducted in a contained continuous flow in-line serial manner. The in-line apparatus depicted schematically in FIG. 4 allows for continuous contained flow through a fluid conduit having a series of in-line mixers interspersed with input ports, including ports that permit entry of the cell suspension from source 43, a cell lysis buffer from source 44, a precipitation buffer from source 47, and, optionally a pH adjustment buffer or neutralization buffer from source 48. The cell suspension, cell lysis, precipitation, and, optionally pH adjustment buffers, are each introduced into the in-line system at controlled rates using a pump in conjunction with a flow meter in the line leading from each of the sources 43, 44, 47 and 48. When the process is primed, the pumps are started essentially simultaneously. Thus, the upstream portion of the system is primed with cell lysis buffer alone while downstream portions of the system further include the addition of precipitation and pH adjustment buffers. Once the system is initiated, it runs continuously until all of the cell suspension has been processed.

Cell Lysis: After priming, the cell suspension is pumped from source 43 at a rate of approximately 2 liters per minute (LPM) into the in-line system where the cell suspension comes into contact with Cell Lysis Buffer (1% SDS w/v, 0.2N NaOH). Cell Lysis Buffer is pumped from source 44 at an approximate ratio of 10 liters per kilogram of initial cell paste and at a rate of approximately 3 LPM. Where SDS:NaOH is employed, the ratio of SDS:NaOH in the lysis solution is controlled to an optimized ratio of 1% SDS:0.2N NaOH with an acceptable variation of ±10% for comparable plasmid yield. The sequence of initiation of the process is in order:

Cell Resuspension pump on, gas inflow on, Cell Lysis Buffer pump on, Precipitation Buffer pump on, and pH Adjustment Buffer pump on.

Introduction of Gas: USP grade nitrogen from source 45 is introduced through a sparge stone 41 disposed in housing 42 into the line communicating the Cell Lysis Buffer to the in-line system. Air has also been shown to be effective in the process and it is likely that other gases, especially those lighter than air, will work also. Hydrogen and oxygen are less desirable for safety reasons in addition to potential problems with oxygen acting as an oxidization agent on the biological material.

Figure 3:
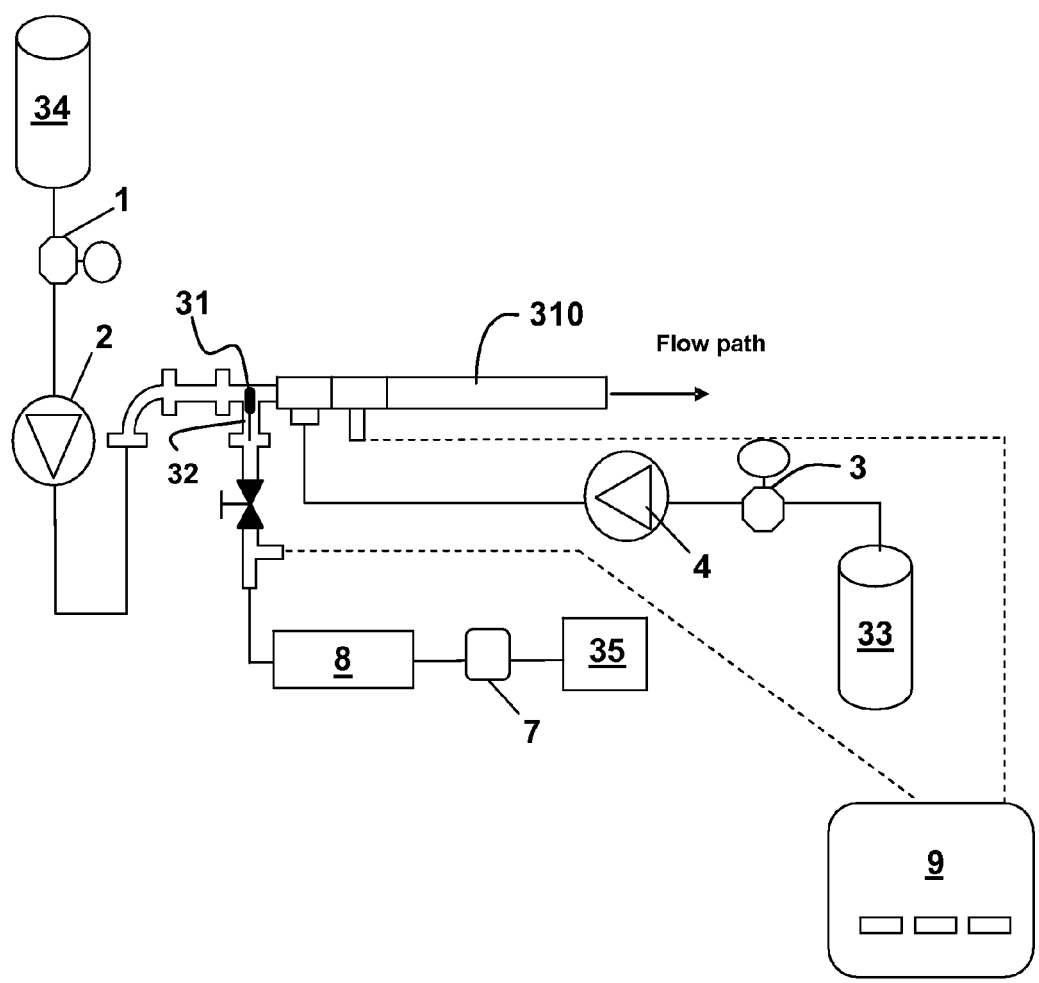
FIG. 3 illustrates the relative placement of a sparge stone in an in-line lysis apparatus according to one embodiment of the present invention.

FIG. 3 provides a schematic depiction of the placement of the gas source in the in-line system. As depicted in FIG. 3, the Cell Lysis buffer is controllably added from source 34 through a flow meter 1 under the action of a pump 2. The gas is provided from air/nitrogen source 35 through regulator 7 under the control of mass flow regulator 8. Pressure box 9 provides monitoring of various the input pressures and flow rates. In the embodiment depicted, the gas enters the Cell Lysis Buffer flow through a sparge stone 31 fixed in housing 32 through which the Cell Lysis Buffer flows prior to entry of the Cell Resuspension into the flow path. The Cell Resuspension is provided from reservoir 33 through a flow meter 3 under the action of a pump 4. In the embodiment depicted, the flow rate is monitored as the combined flow of the Cell Resuspension and Cell Lysis Buffer together with entrained air enters the first of a set of static mixers 310.

FIG. 1 provides a diagram of the sparge stone 11 fixedly placed in housing 12 in accordance with one embodiment of the invention. In this embodiment the sparge stone 11 is approximately 3 inches long and approximately ⅜ of an inch in diameter and is fixed mounted in housing 12 by a compression clamp. In this embodiment, the sparge stone 11 is stainless steel and has approximately 2 micron holes through which the nitrogen passes thus forming bubbles of a controlled size upon contacting the Cell Lysis Buffer. In this embodiment, the sparge stone 11 is placed upright in-line in the housing 12. The housing 12 is placed in a line leading from a reservoir holding the Cell Lysis Buffer at a point just prior to the point at which the Cell Resuspension is introduced. Nitrogen is added at a rate of 0.99 L/min through the sparge stone 11.

Precipitation pH Adjustment and Clarification: As depicted in FIG. 4, the Cell Resuspension and Cell Lysis Buffer containing entrained nitrogen bubbles of defined size flows together in-line through a series of in-line static mixers 410 thus effecting mixture with, and lysis of, the cells. The flow rate is approximately 0.3 linear feet per second (ft/sec). Precipitation buffer (3M potassium acetate, 2M acetic acid, pH 5.5; at a ratio of 5 liters per kilogram of cell paste) from source 47 is added in-line to precipitate cell debris, and the mixture continues to flow through a second set of static mixers 411. pH Adjustment Buffer (2.5 M Tris, 4-5 liters per kilogram of cell paste) is added in-line from source 48 to adjust the pH of the lysate, which then flows through a short static mixer 10 before collection into Lysate Clarification Tank 52. Each solution is added at a controlled flow rate, with the initial linear flow rate through the mixers kept at approximately 0.3 ft/sec, which increases to as much as approximately 1.1 ft/sec as further volumes are added with addition of the Precipitation and pH Adjustment Buffers. The flow rate of each solution into the static mixers can be varied ±10% with no detectable effect on plasmid yield or purity.

The unclarified precipitated and neutralized lysate is allowed to flow gently into the bottom of the Lysate Clarification Tank 52. The lysate is allowed to separate for 1-2 hours at ambient temperature. The floating precipitate/flocculent 50 rises to the top of the tank due to the air bubbles introduced to the mixture and overlies a substantially clear fluid representing a clarified lysate. The floating precipitate 50 forms quickly but is allowed to rest for a period of 1-2 hours in order to coalesce and solidify. The underlying clarified lysate 51 is removed from the bottom of tank 52 either by pumping through a dip tube 54 or, optionally, by draining through a bottom port 53.

The clarified lysate 51 obtained as the clear liquid underlying the floating flocculent is further purified by filtration a series of filters 55 to generate a filtered lysate that can be subject to further purification if desired. In one embodiment the filter series 55 is a follows: a 8 micron depth filter (Seitz Bio-40, 170 L/m$^2$ capacity), a 2 micron depth filter (Seitz Bio-10, 170 L/m$^2$ capacity), a 1.2 micron pre-filter (1.2 micron glass fiber absolute filter, Sartorius, GF2, 5 L/ft$^2$ capacity) and 0.2 micron nominal filter (0.2 micron nylon absolute filter, Sartorius or Pall-Gelman N$_{66}$, 5 L/ft$^2$ capacity) in series. The flow rate is 0.2 L/min/ft$^2$, based on the area of the smaller of the pre-filter or the 0.2 micron filter, using a peristaltic pump, capable of 0.2 L/min/ft$^2$ of 0.2 micron filter at 10 psig. Lysate capacity of the prefilter and 0.2 micron filter is 5 L/ft$^2$. Filtration is continued until the introduction of precipitate causes a pressure of >10 psi over the Bio-40, at which time that filter is removed from the train and the remaining lysate in the filter housings is recovered.

Alternatively, the clarified lysate can be filtered through a Miracloth. The pH and conductivity of the Miracloth filtered lysate is measured. If the filtered lysate pH is below 8.0, it is adjusted with 2.5 M Tris buffer. If the conductivity is greater than 60 mS/cm, it is adjusted with purified water. The Miracloth filtered lysate is pumped through a 1.2 micron Glass fiber (GF2) filter in tandem with a 0.2 micron Nylon filter. The volume of Miracloth filtered lysate that can go through both filters is 5 liter per ft$^2$ per filter. The pump flow rate through the filter is 0.2 liter per minute per ft$^2$ with a pressure drop no greater than 10 psi per filter.

The filtered lysate may be held at ambient temperature for 24 hours or at 2-8° C. for up to 1 week prior to initiating the next process step. Filtered product cannot be frozen because of precipitate formation or aggregation of small particle size upon thawing. These require re-filtration of the product before processing can continue. Anion exchange HPLC chromatography is used to estimate the plasmid DNA concentration in process samples. A peak area standard curve delineates an approximation of the amount of supercoiled DNA and open circular DNA present in the sample.

Anion Exchange Chromatography: An anion exchange resin, Trimethylaminoethyl Fractogel 650M (Merck/EM Separations) is used to separate intact plasmid DNA from plasmid impurities and host impurities such as residual protein, endotoxin, chromosomal DNA and digested RNA. The column is equilibrated with an Equilibration Buffer: 50 mM Tris, 0.55 M NaCl, pH 8.5. Most of the impurities do not bind to the resin or are removed from the column by sequential washes of increasing salt concentration, starting with the Equilibration Buffer. More tightly bound components are washed off with a buffer of higher salt concentration [50 mM Tris, 0.65 M NaCl, pH 8.5]. The plasmid DNA is eluted from the column with a yet higher salt concentration [50 mM Tris, 0.71 M NaCl, pH 8.5]. The eluent is filtered through a 1.2 micron glass fiber filter (Sartorius, 1 ft$^2$ membrane per g pDNA) and then a 0.2 micron nylon filter, (Sartorius or Pall-Gelman N$_{66}$, 1 ft$^2$ membrane per g pDNA), into an irradiated container. The column eluent may be held for no longer than 1 week at 2-8° C. prior to further processing. The exact salt concentration used for the above buffers is established during resin acceptance testing of each lot of resin to compensate for the variation in charge density of the resin from lot to lot. The concentration typically varies ±0.05M NaCl.

Ultrafiltration/Diafiltration: Ultrafiltration and diafiltration are used to concentrate, clear small molecular weight components, and to exchange the ion exchange column eluent into a 10 mM Tris, pH 8.0 buffer for formulation. A description of the use of ultrafiltration in conjunction with in-line lysis and ion exchange chromatography is provided in Dang, Bussey and Bridenbaugh, WO 00/05358, incorporated herein by reference. In the present embodiment, ultrafiltration is employed following ion exchange chromatography. Typically ultrafiltration is carried out essentially as described in Bussey et al., U.S. Pat. No. 6,011,148, incorporated herein by reference.

Ultrafiltration (UF): A open screen tangential flow ultrafiltration cassette is used together with a modified polyethersulfone based, 50,000 Dalton molecular weight cutoff ultrafiltration membrane chosen for its capacity to retain plasmid DNA and pass small molecules. The filtered ion exchange eluate is connected to the UF feed line. The UF/DF system is operated at 0.5-1.0 L per minute per ft$^2$ with a TMP of 2-4 psig. When necessary, the flow rate is lowered to maintain a TMP of 2-4 psig. The permeate valve is opened and the permeate line is directed into the filtered ion exchange pool. This material is recirculated through the system to build a gel layer for 20-30 minutes at TMP 2-4 psig. A gel layer is built when permeate UV$_{260}$ nm is less than 0.1 mg/ml DNA through the permeate line. Without stopping the pump, the permeate line is directed to drain and the plasmid DNA is concentrated until a concentration of ≧3 mg/mL is achieved before proceeding to the diafiltration step.

Diafiltration (DF): Without shutting off the pump, diafiltration buffer (10 mM Tris, pH 8.0) is fed into the recirculation tank. The plasmid DNA is concentrated, diafiltered to achieve a conductivity of less than 0.8 mS/cm at 25° C. or equal to the diafiltration buffer conductivity (typically 8 to 12 DF volumes) and then concentrated to >2 mg/ml, as necessary. The diafiltered concentrate is immediately processed. If necessary, ultrafiltration may be continued until a target concentration of ≧3 mg/mL is achieved.

Final Filtration: The UF/DF plasmid DNA Pool is filtered through a 0.2 micron filter at 0.01 to 0.02 mL/min/cm$^2$ into a sterile container.

The examples and embodiments described herein are for illustrative purposes only, and various modifications will be apparent to those of skill in the art, the invention to be limited only by the scope of the appended claims. All publications, patents and patent applications cited herein are hereby incorporated by reference as if set forth in their entirety herein.

We claim:

1. A continuous flow pharmaceutical grade apparatus for lysing bacterial cells comprising a fluid flow path comprising and in fluid communication with:

a cell lysis buffer conduit and inlet for introduction of a cell lysis buffer into the fluid flow path;

a gas introduction port comprising an aperture for introducing a controlled flow of gas into the fluid path;

a cell suspension conduit and inlet for introducing a bacterial cell suspension into the fluid path;

a first in-line mixer disposed in-line in the fluid flow path at a location after the cell lysis buffer inlet, the gas introduction port, and the cell suspension inlet, wherein the first in-line mixer is adapted for combining the bacterial cell suspension, cell lysis buffer and gas, thereby forming a cell lysate;

a precipitation buffer conduit and inlet disposed in-line in the fluid flow path at a location after the first in-line mixer, and adapted for introducing a precipitation buffer into the cell lysate;

a second in-line mixer disposed in-line in the fluid flow path at a location after the precipitation buffer inlet, and adapted for combining the cell lysate with the precipitation buffer thereby forming a precipitated lysate; and a lysate clarification tank in fluid communication with the fluid flow path and positioned and configured to receive and rest the precipitated lysate for flotation and separation of a precipitate phase from a clarified lysate phase by resting, coalescence and solidification of the precipitate phase.

2. The apparatus of claim 1, wherein either or both of the first in-line mixer and the second in-line mixer comprise at least one internal static mixing element.

3. The apparatus of claim 1, wherein the aperture comprises a sparge stone or a disk filter having a plurality of pores of an average diameter of less than approximately 5 microns.

4. The apparatus of claim 1, further comprising a pH adjustment conduit and inlet for introducing a pH adjustment buffer into the precipitated lysate and a third in-line mixer disposed in-line in the fluid flow path after the second in-line mixer, and adapted for combining the pH adjustment buffer and the precipitated lysate prior to flowing into the lysate clarification tank.

5. The apparatus of claim 1, further comprising a collection conduit and outlet for collecting the clarified lysate from a bottom of the lysate clarification tank and a series of filters downstream of, and in fluid communication with, the collection conduit.

6. The apparatus of claim 5, further comprising at least one anion exchange column downstream of, and in fluid communication with, the series of filters.

7. The apparatus of claim 5, wherein the series of filters includes at least one glass fiber filter and at least one nylon filter.

8. The apparatus of claim 1, wherein the aperture for introducing a controlled flow of gas into the cell lysis buffer comprises a plurality of pores.

9. The apparatus of claim 1, wherein the aperture comprises a sparge stone or disk filter comprising pores having an approximate average diameter of 2 microns or less.

10. The apparatus of claim 9, wherein the aperture is a stainless steel sparge stone.

* * * * *